United States Patent [19]
Coe

[11] Patent Number: 5,305,365
[45] Date of Patent: Apr. 19, 1994

[54] MAMMOGRAPHY SYSTEM WITH REARWARDLY TILTING MAMMOGRAPH

[75] Inventor: Robert P. Coe, Dix Hills, N.Y.

[73] Assignee: Bennett X-Ray Technologies, Copaigue, N.Y.

[21] Appl. No.: 980,776

[22] Filed: Nov. 24, 1992

[51] Int. Cl.$^5$ .............................................. A61B 6/04
[52] U.S. Cl. ...................................... 378/37; 378/195; 378/208
[58] Field of Search ................. 378/37, 204, 208, 180, 378/195

[56] References Cited

U.S. PATENT DOCUMENTS

| | | | |
|---|---|---|---|
| 3,556,081 | 1/1971 | Jones | 378/208 |
| 3,578,971 | 5/1971 | Lasky | 378/180 |
| 3,824,397 | 7/1974 | Bauer et al. | 378/37 |
| 4,618,973 | 10/1986 | Lasky | 378/37 |

Primary Examiner—David P. Porta
Attorney, Agent, or Firm—Meltzer, Lippe, Goldstein, Wolf, Schlissel & Sazer

[57] ABSTRACT

A mammography system with a variable angle, rearwardly tilting mammograph adjustable to individual, standing or sitting patients in forwardly leaning posture to maximize breast tissue exposure to the mammograph by gravity. The invention covers both the mammograph machine and the mammography method.

10 Claims, 6 Drawing Sheets

MAMMOGRAPHY SYSTEM WITH REARWARDLY TILTING MAMMOGRAPH

BACKGROUND OF THE INVENTION

1. Field of the Invention

The field of x-ray and other imaging systems as applied to the detection and location of cancers and other tumors of the breast.

2. Description of the Prior Art

The closest prior patent art known to applicant consists of the following U.S. patents:

| | |
|---|---|
| 3,365,575 | Strax |
| 3,530,293 | Wehmer |
| 3,556,081 | Jones |
| 3,578,971 | Lasky |
| 3,609,355 | Schwarzer |
| 3,636,349 | Faude et al |
| 3,824,397 | Bauer et al |
| 3,973,126 | Redington et al |
| 3,991,316 | Schmidt et al |
| 4,097,748 | Monvoisin |
| 4,259,585 | Novak et al |
| 4,599,738 | Panetta et al |
| 4,910,756 | Mikkonen et al |
| 4,926,453 | Toniolo |
| 4,979,196 | Lieutaud et al |
| 5,078,142 | Siczek et al |

Of these patents, the most pertinent is believed to be U.S. Pat. No. 3,824,397 issued to Bauer et al. As stated in the Bauer specification, column 1, first three paragraphs, the Bauer invention is of a device of x-ray mammography wherein the support for the x-ray tube and the film table "can be tilted with respect to the horizontal arm about an axis which is perpendicular to the axis of this arm" As stated in Column 2, lines 24, 25, the photography device is shown (FIG. 3) "in a tilted forward position".

There is no suggestion in Bauer that the x-ray tube and film table assembly can or should be tilted in rearward direction, since this would conflict with the purpose of moving "the entire photography 4 towards the patient" (Column 2, lines 13, 14).

Another prior art patent that is pertinent to the present invention is Siczek et al., U.S. Pat. No. 5,078,142. This patent utilizes gravity to maximize exposure of the patient's breast to an x-ray beam, but it requires that the patient, or at least the upper part of the patient's body, lie prone on a specially designed table, see FIGS. 1A and 2 thereof.

Lasky U.S. Pat. No. 3,578,971 shows a patient bent over to the extent that the breast "is in a vertical suspended position" (Column 2, lines 23,24) being held in that position between "vertical walls 20 and 22" (Column 2, lines 36-39). This appears to be equivalent to the prone position of the patient in FIG. 2 of the Siczek patent.

The present invention differs from the Bauer et al. patent in that the mammograph of the present invention does not tilt forwardly for a mammography procedure. The present invention differs from the Siczek et al. and Lasky patents in that it enables the patient to stand or sit in front of the mammograph while leaning forwardly within a relatively comfortable angular range into operative mammography position.

SUMMARY OF THE INVENTION

The mammograph of the present invention is tiltably mounted on a suitable column or other supporting structure, the tilting direction being rearward, the tilting axis being horizontal, in front of the patient, and extending laterally from one side to the other of the patient. The angular tilting range of the mammograph is approximately 90 degrees from vertical to cover the range of 15-25 degrees corresponding to the angular forward leaning range of patients. This 15-25 degree tilting and leaning range is believed to be an optimum range to accommodate the contour and posture characteristics of individual patients in order to maximize breast tissue exposure to the mammograph by gravitational suspension of the breasts angularly away from the body of the patient. This tilting and leaning range is especially helpful to difficult patients, such as kyphotic, barrel-chested and wheelchair-bound patients.

The mammograph of the present invention is also rotatable about an axis that varies with the tilt axis and is perpendicular to the tilt axis and varies with the tilt angle.

The mammograph of the present invention is also provided with a special geometric relationship between the x-ray tube and the film plane. This geometric relationship, combined with the variable tilt function, allows the technologist positioning capabilities which were previously impossible.

This tilting of the mammograph arm to the proper position of the patient increases the amount of breast tissue, and separates glandular tissue, for more accurate diagnosis.

When the patient is relaxed, the pectoral muscle is relaxed and the breast becomes more mobile. One of the most important things a technologist can do is to relax the patient. When the patient stiffens up, the entire mobility of the breast is lost. One of the reasons mammography can be done as well as it is done is because the breast is a mobile appendage, but as soon as the patient tightens up, this advantage is lost. The fact that the patient can be made more comfortable will allow the breast to be more mobile, allowing the technologist to position the breast more easily.

The objective of any mammogram is to get the entire breast in profile—to get as much tissue as possible on the film. A doctor cannot diagnose what he doesn't see and if he does not get the entire breast on film there is always a chance that he has missed something. What this new tilting action does is to allow the technologist to get more breast tissue on the film.

DESCRIPTION OF THE PREFERRED EMBODIMENT

Mammograph 10 is an imaging device designed primarily for x-ray examination of breast tissues. It should be understood that the invention is equally applicable to other imaging systems used in mammography, and except where otherwise indicated, as used in the claims, "mammograph" and "mammography" are not limited to x-ray imaging devices or systems.

Mammograph 10 comprises, essentially, a mammography system arm 12, an imaging device, in this embodiment an x-ray tube 14, mounted at the upper end of said arm, and a film receptor 16 mounted opposite said imaging device adjacent the lower end of said arm. A breast compression paddle 18 is adjustable mounted on arm 12 above the film receptor 16, said paddle being oriented in parallel relation to the film plane and being adjustable along an axis perpendicular to the film plane.

The mammograph assembly is mounted on vertical support column 20 by support means enabling the mammograph to move in three directional modes: linearly in both vertical directions, angularly about a horizontal axis, and rotatably about an axis perpendicular to said horizontal axis.

Figure 2:
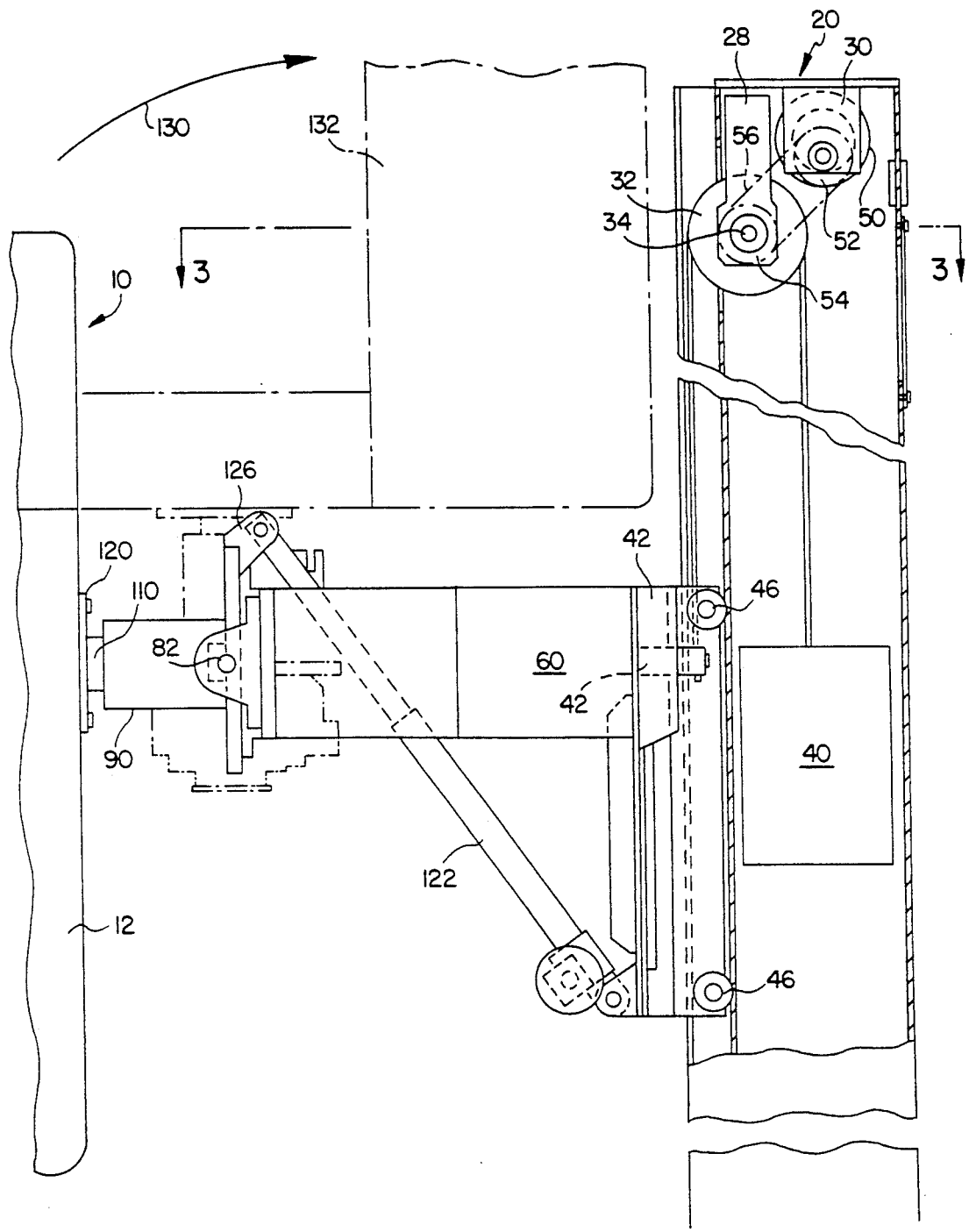
FIG. 2 is an enlarged side view, partly in vertical section, showing the adjustable tilting mechanism of the present invention.
Figure 3:
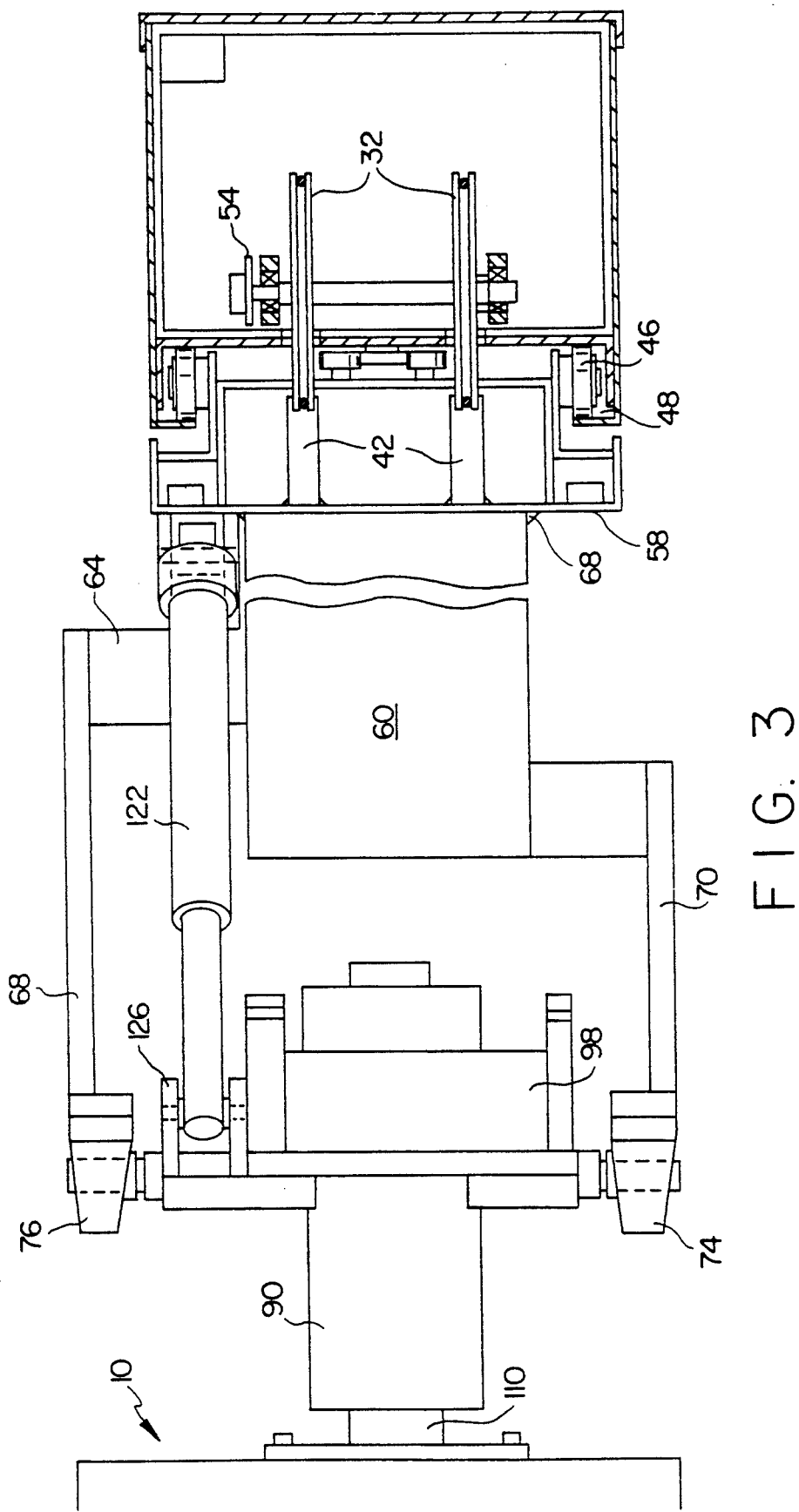
FIG. 3 is a top view showing the adjustable tilting mechanism, and showing the supporting column in horizontal section on the line 3—3 of FIG. 2.

Referring first to support column 20, it will be observed in FIGS. 2 and 3 that it is a hollow column mounted on a base 22 standing on a floor 24. Secured to the top of column 20 is a mounting plate 26 which supports brackets 28 and 30. Pulleys 32 are rotatably mounted on bracket 28 by means of bearings 36 supporting shaft 34. Suspended on pulleys 32 are cables 38. At one end, these cables are attached to a counterweight 40, and at the opposite end, the cables are attached to brackets 42 secured to carrier frame 44. The carrier frame is adapted to move vertically on the front wall of column 20 by means of wheels 46 mounted on said carrier frame and riding in vertical channels or tracks 48.

Bracket 30 supports a reversible motor 50 equipped with speed reduction gears through which it drives a sprocket 52. A second sprocket 54 secured to shaft 34 of the pulleys is connected to and driven by sprocket 52 by means of a sprocket chain 56. When the motor is energized to operate in one direction it raises the counterweight while lowering the carrier frame. When energized to operate in the opposite direction, the motor rises the carrier frame while allowing the counterweight to move downwardly by gravity. A standard brake (not shown) is provided to control this operation.

Carrier frame 44 includes a vertical mounting plate 58 that supports the supporting arm 60 of the mammograph. Supporting arm 60, in the present embodiment, is a 6 inch by 6 inch tube that is secured in perpendicular relation to mounting plate 58, as by welds 62. Extending laterally from arm 60 is a pair of brackets 64, 66 which support bars 68 and 70 respectively. Bars 68 and 70, at their free ends, support bearing blocks 72 and 74 and their respective bearings 76 and 78. Carried by bearings 76 and 78 are coaxial stud shafts 80 and 82 which define the tilting axis of the mammograph.

Figure 4:
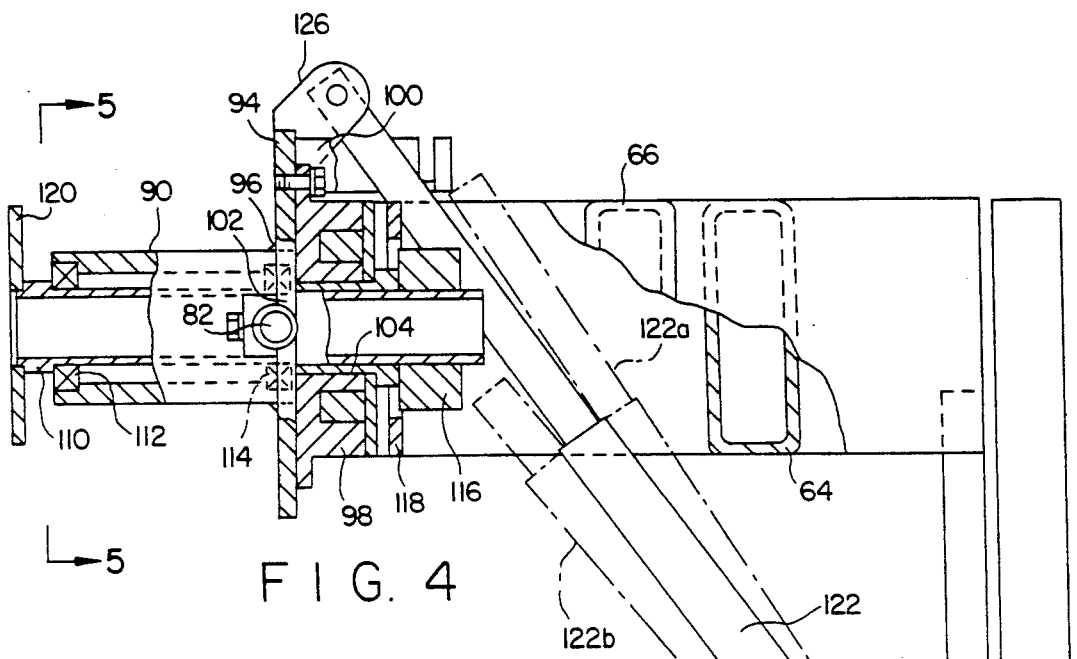
FIG. 4 is a side view, partly in vertical section, of the rotating and tilting support for the mammograph.
Figure 5:
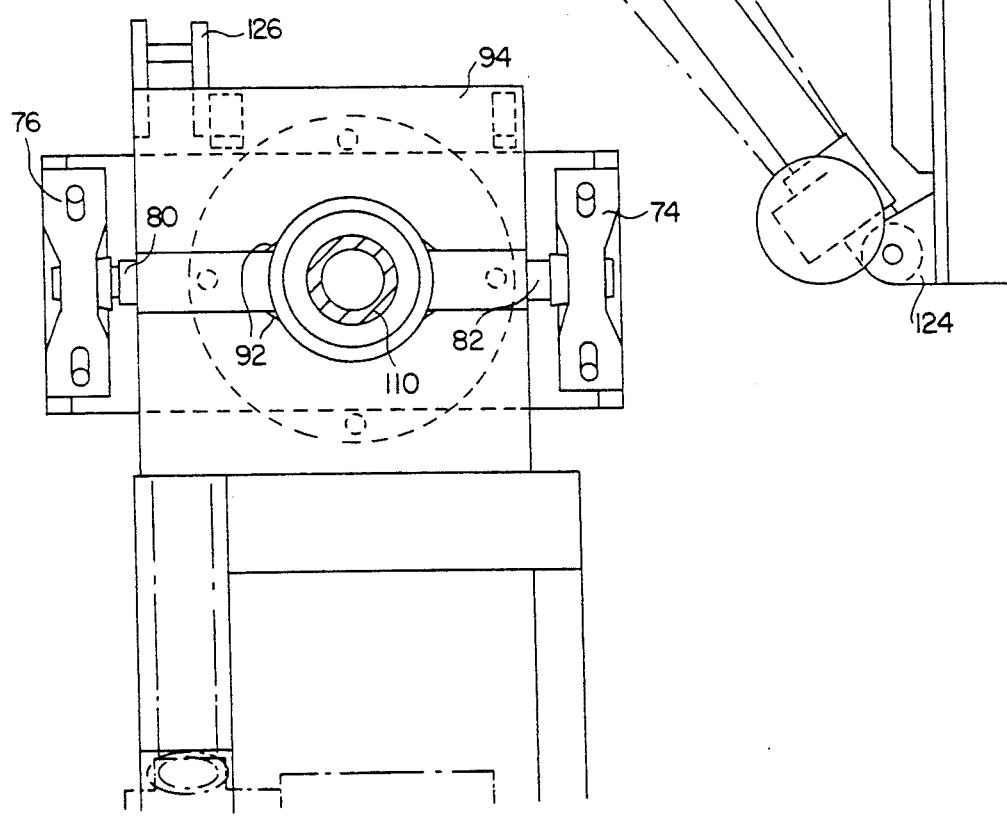
FIG. 5 is a vertical section on the line 5—5 of FIG. 4.

It will be seen in FIGS. 4 and 5 that the stud shafts are secured to an outer tube 90 as by welds 92 and that said outer tube is secured to plate 94 as by welds 96. An annular block 98 is secured to plate 94 as by means of bolts 100. Plate 94 has a cylindrical hole 102 formed therein in axial alignment with said block. Structurally and functionally, stud shafts 80 and 82, outer tube 90, plate 94 and annular block 98 constitute a single integral assembly rotatably supported by another structural and functional assembly comprising bearings 76, 78, supporting bars 68, 70, brackets 64, 66 and tubular arm 60 which is welded to vertical mounting plate 58.

Extending coaxially through outer tube 90, plate 94 and annular block 98 is an inner tube 110 which is rotatably supported in said outer tube 90 by means of bearings 112, 114. Inner tube 110 is free to rotate but it is fixed against axial displacement by bearing 112 at one end and a collar 116 abutting against a stop member 118 at the opposite end.

At its forward end, inner tuber 110 is secured to a mounting plate 120 which is itself attached to the mammograph itself. See FIGS. 1 and 2. This is the support for the mammograph and for its pivotal capability as will now be described.

Figure 1:
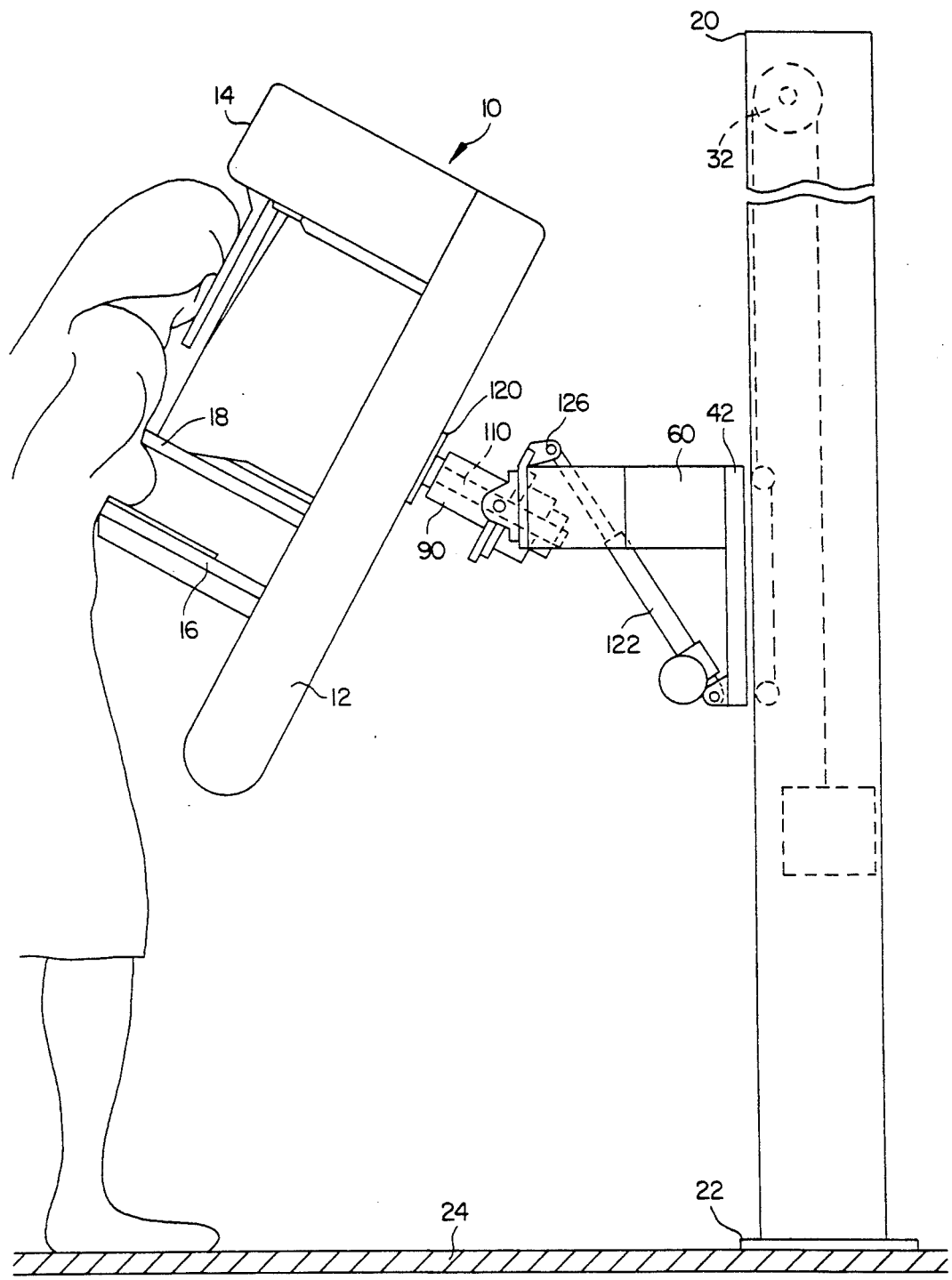
FIG. 1 is a side view of the mammograph comprising the present invention, showing it in operative position in connection with a standing patient.

Referring again to FIGS. 4 and 5, it will be seen that a motorized ball drive actuator 122 is pivotally secured at its lower end to a bracket 134 on mounting plate 58 of carrier frame 44. At its upper end actuator 122 is pivotally secured to a bracket 126 on plate 94. As shown in FIG. 1 and by phantom lines 122a and 122b in FIG. 4, when actuator 122 is operated in conventional manner, it causes the plate 94, annular block 98 and outer tube 90 assembly to tilt rearwardly from the vertical, the optimum range of tilt being about 15-25 degrees. And since inner tube 110 is held within outer tube 90 by means of bearings 112, 114 and collar 116, the tilting action of said assembly is translated into a corresponding tilting action of the mammograph. See arrow 130 and phantom lines 132 in FIG. 2.

Figure 6:
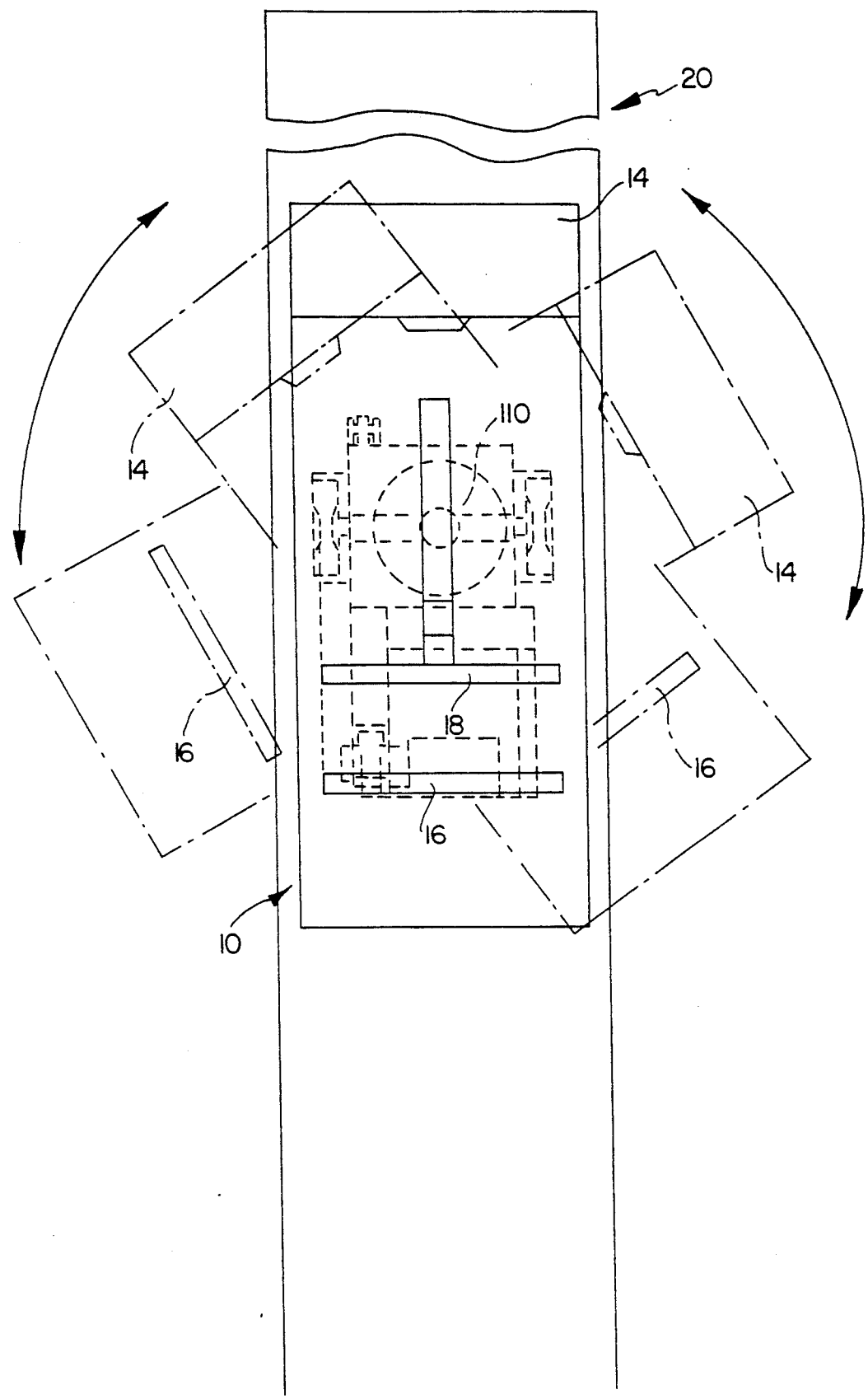
FIG. 6 is a view of the rotational capability of the mammograph.

There is another operation which the mammograph is capable of performing and that is rotation about the common axis of outer tube 90 and inner tube 110. This is illustrated in FIG. 6. The rotary drive (not shown) for this operation is conventional.

It will now be apparent that the mammograph of the present invention is capable of vertical adjustment by means of carrier frame 44, tiltable adjustment by means of actuator 122, and rotational adjustment about the axis of inner and outer tubes 90 and 110 respectively. Each of these adjustments is independent of the others and may be made without affecting the other adjustments. But functionally they operate in combination to adjust the mammograph to produce optimum results with maximum comfort to the patient.

Thus, the patient may stand as shown in FIG. 1, or sit on a chair, and lean forwardly to maximize breast exposure to the imaging head of the mammograph. The tilt of the mammograph can be adjusted to the angle best suited for imaging the breasts of individual patients. And the mammograph can be adjusted rotationally without disturbing the optimal tilt position set for the patient.

Figure 7:
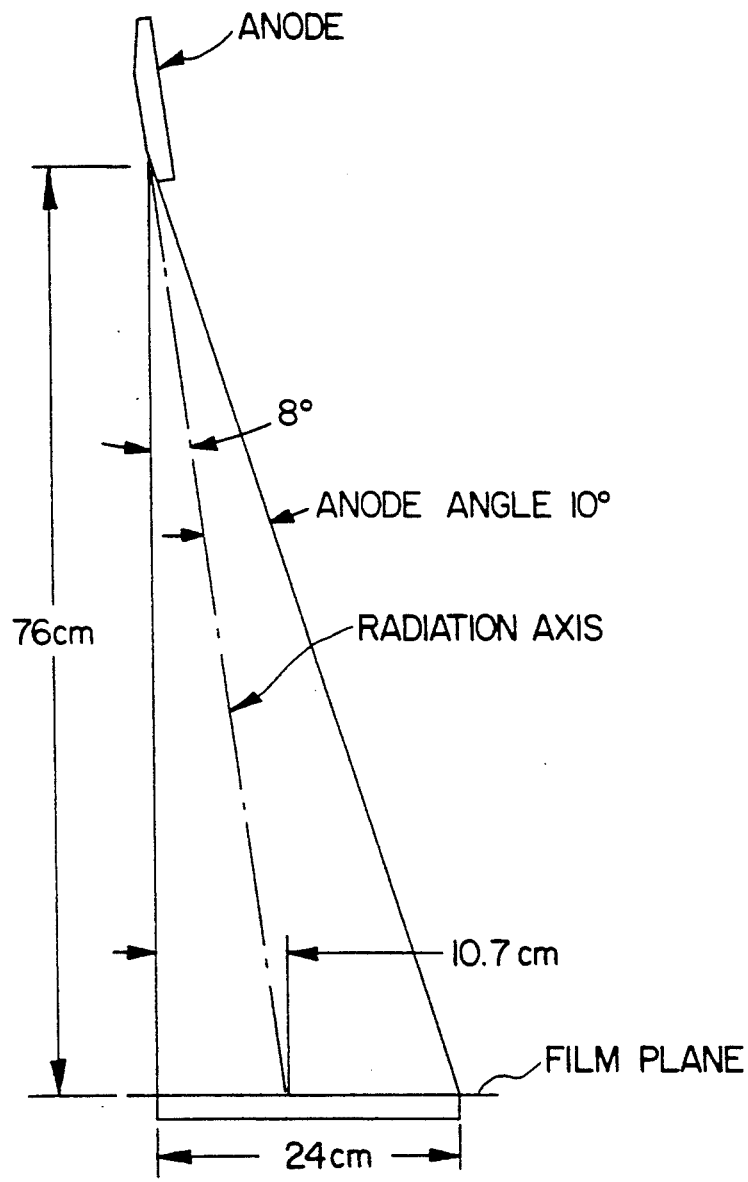
FIG. 7 is a schematic diagram of the geometry of the x-ray imaging system of the mammograph.

One setting remains constant in all of the foregoing adjustments and that is the setting of the system's geometry as shown in FIG. 7. It is the combination of this geometry—distance of the anode of the x-ray tube to the film plane of the film receptor on a line perpendicular to the film plane 76 cm., radiation axis, 8 degrees from said perpendicular line, anode angle 10 degrees from the radiation axis—with the tilting range of about 15-25 degrees rearwardly from vertical and rotational adjustment that allows the technologist positioning capabilities that were previously impossible.

It will now be evident that the mammographic method of the present invention comprises a joint effort by the patient and the technologist, whereby the patient indicates her range of comfort postures (the forward leaning angle) and the technologist determines the range of optimum imaging positions (the rearward tilt angle). This angle depends on shape and gravitational pendularity of patient. The rotational angle depends on the angle of pectoral muscle.

The steps of this joint effort, in essence, are these:

a. The mammograph is tilted by the technician to a rearward angular position (within a range of about 15-25 degrees to vertical) deemed best suited for optimum breast exposure of the individual patient.

b. The patient is caused to lean forwardly for placement of her breast on the tilted film receptor.

c. If the patient's position is not reasonably comfortable, the rearward tilt of the mammograph is adjusted to her comfort within said 15-25 degree range.

d. The patient's position being reasonably comfortable, the compression paddle is lowered onto the breast with appropriate pressure applied.

e. The imaging then proceeds.

f. Rotational adjustment of the mammograph may take place for additional imaging.

The foregoing is illustrative of the principles of the invention and of a preferred embodiment thereof. Modified embodiments that are within the scope of these principles and of the claims are encompassed within the intended scope of the invention.

I claim:

1. A mammography system, comprising:
   a. a mammograph,
   b. a mammograph support stand,
   c. a first mount supported on said support stand for vertical movement in a first vertical plane,
   d. a second mount supported on said first mount for angular movement about a horizontal axis in a second vertical plane parallel to the first vertical plane,
   e. said angular movement, above said horizontal axis, being toward said first vertical plane, and
   f. a third mount supported on said second mount for rotational movement about an axis perpendicular to said horizontal axis,
   g. said mammograph being mounted on said third mount,
   h. whereby the mammograph is rearwardly tiltable about said horizontal axis, rotatably adjustable about said perpendicular axis, and vertically adjustable with said first mount.

2. A mammograph system in accordance with claim 1 wherein:
   a. the mammograph comprises a supporting arm,
   b. an x-ray tube at the upper end of said arm,
   c. a film receptor adjacent the lower end of said arm, and
   d. a breast compressor adjustably mounted on said arm above said film receptor and relative thereto.

3. A mammography system in accordance with claim 2, wherein:
   a. the distance from the anode of the x-ray tube to the film plane of the film receptor, on a line perpendicular to the film plane is 76 cm., and
   b. the radiation axis is 8 degrees from said perpendicular line.

4. A mammography system in accordance with claim 3, wherein the anode angle is 10 degrees from the radiation axis.

5. A mammography system in accordance with claim 1, wherein:
   a. a power drive is provided between said mammograph support stand and said first mount to drive said first mount in either vertical direction, and
   b. a power drive is provided between said first mount and said second mount to drive said second mount in either angular direction about said horizontal axis within said range of about 15-25 degrees.

6. A mammography system in accordance with claim 1, wherein:
   said angular movement extends within a range of approximately 15-25 degrees.

7. A mammography imaging method, comprising the steps of:
   a. tilting a mammograph rearwardly from vertical,
   b. causing a patient to lean forwardly to a comfortable position with respect to the film receptor of the mammograph,
   c. positioning and compressing the breasts on the film receptor, and
   d. imaging the breasts.

8. A mammography system, comprising
   a mammograph,
   a mammograph support stand,
   a mount connecting said mammograph to said mammograph support stand,
   said mount permitting rearward tilting of said mammograph toward said mammograph support stand.

9. The mammography system of claim 6 wherein said rearward tilting is within a range of approximately 15°-25°.

10. The mammography system of claim 6 wherein said mount comprises a tilting arm which is connected at a first end to said mammograph and at a second end to said mammograph stand.

* * * * *